(12) United States Patent
Kiele et al.

(10) Patent No.: US 11,785,716 B2
(45) Date of Patent: Oct. 10, 2023

(54) IMPLANTABLE ELECTRICAL CONNECTING DEVICE

(71) Applicant: Albert-Ludwigs-Universität Freiburg, Freiburg (DE)

(72) Inventors: Patrick Kiele, Freiburg (DE); Eva Singler, Breisach (DE); Thomas Stieglitz, Freiburg (DE); Juan Sebastian Ordonez, Ghent (BE)

(73) Assignee: Albert-Ludwigs-Universität Freiburg, Freiburg (DE)

( * ) Notice: Subject to any disclaimer, the term of this patent is extended or adjusted under 35 U.S.C. 154(b) by 156 days.

(21) Appl. No.: 17/325,695

(22) Filed: May 20, 2021

(65) Prior Publication Data

US 2021/0274654 A1 Sep. 2, 2021

Related U.S. Application Data

(63) Continuation of application No. PCT/EP2019/081629, filed on Nov. 18, 2019.

(30) Foreign Application Priority Data

Nov. 21, 2018 (DE) ..................... 10 2018 219 917.5

(51) Int. Cl.
*H05K 1/11* (2006.01)
*H01R 12/77* (2011.01)
(Continued)

(52) U.S. Cl.
CPC ........... *H05K 1/118* (2013.01); *H01R 12/777* (2013.01); *H01R 12/778* (2013.01); *H01R 12/78* (2013.01);
(Continued)

(58) Field of Classification Search
CPC .... H01R 12/61; H01R 12/777; H01R 12/778; H01R 12/78; H01R 43/26; H01R 2201/12;
(Continued)

(56) References Cited

U.S. PATENT DOCUMENTS 5,213,511 A * 5/1993 Sobhani .................. H01R 12/62
439/492
5,743,747 A * 4/1998 Sobhani ............... H05K 3/4007
439/492

(Continued)

FOREIGN PATENT DOCUMENTS

DE 10 2017 208 625 B3 11/2018

OTHER PUBLICATIONS

E. Letechipia, P. H. Peckham, M. Gazdik, and B. Smith, "In-Line lead connector for use with implanted neuroprosthesis," "IEEE Trans. Biomed" Engl., vol. 38, No. 7, pp. 707-709, 1991.

(Continued)

*Primary Examiner* — Gary F Pau Men
(74) *Attorney, Agent, or Firm* — Barley Snyder

(57) ABSTRACT

An implantable electrical connecting device includes a first elastic multi-ply layer and a second elastic multi-ply layer. The first elastic multi-ply layer has a first electrically conductive layer and a plurality of first electrical contacts electrically conductively connected to the first electrically conductive layer of the first elastic multi-ply layer. The second elastic multi-ply layer has a first electrically conductive layer and a plurality of second electrical contacts electrically conductively connected to the first electrically conductive layer of the second elastic multi-ply layer. The second electrical contacts make contact with the first electrical contacts.

22 Claims, 7 Drawing Sheets

(51) Int. Cl.
*H01R 12/78* (2011.01)
*H01R 43/26* (2006.01)
*H05K 3/14* (2006.01)
*A61N 1/375* (2006.01)
*H05K 3/00* (2006.01)

(52) U.S. Cl.
CPC ............ *H01R 43/26* (2013.01); *H05K 3/146* (2013.01); *A61N 1/3752* (2013.01); *H01R 2201/12* (2013.01); *H05K 3/0029* (2013.01); *H05K 3/0035* (2013.01); *H05K 2201/09754* (2013.01)

(58) Field of Classification Search
CPC ...... H05K 1/118; H05K 3/146; H05K 3/0029; H05K 3/0035; H05K 2201/09754; A61N 1/3752
USPC .......................................................... 439/67
See application file for complete search history.

(56) References Cited

U.S. PATENT DOCUMENTS

| | | | |
|---|---|---|---|
| 6,368,147 B1 | 4/2002 | Swanson | |
| 8,192,207 B2* | 6/2012 | Iida | H05K 3/365 439/67 |
| 8,267,700 B2* | 9/2012 | Mizoguchi | H01R 12/613 439/67 |
| 8,465,328 B2* | 6/2013 | Iida | H01R 4/58 439/660 |
| 8,708,712 B2* | 4/2014 | Iida | H01R 12/79 439/67 |
| 9,795,787 B2* | 10/2017 | Cho | A61N 1/0543 |
| 2006/0068613 A1* | 3/2006 | Tsukada | H05K 1/028 439/67 |
| 2012/0149246 A1 | 6/2012 | Iida et al. | |
| 2013/0344712 A1* | 12/2013 | Kole | H05K 3/365 439/67 |
| 2016/0235989 A1 | 8/2016 | Cho et al. | |

OTHER PUBLICATIONS

M. Cocco, P. Dario, M. Toro, P. Pastacaldi, and R. Sacchetti, "An implantable neural connector incorporating microfabricated components," "J. Micromech. Microeng ", vol. 3, No. 4, pp. 219-221, 1993.

R. G. Hauser and B. J. Maron, "Lessons from the failure and recall of an implantable cardioverterdefibrillator," (Engl), "Circulation", vol. 112, No. 13, pp. 2040-2042, 2005.

Abstract of DE 102017208625B3, dated Nov. 15, 2018, 2 pages.

* cited by examiner

IMPLANTABLE ELECTRICAL CONNECTING DEVICE

CROSS-REFERENCE TO RELATED APPLICATIONS

This application is a continuation of PCT International Application No. PCT/EP2019/081629, filed on Nov. 18, 2019, which claims priority under 35 U.S.C. § 119 to German Patent Application No. 102018219917.5, filed on Nov. 21, 2018.

FIELD OF THE INVENTION

The present invention relates to an electrical connecting device and, more particularly, to an implantable electrical connecting device.

BACKGROUND

Implantable connecting devices (hereinafter also referred to as connectors) are an important issue in the manufacture and implantation of active implantable medical devices (AIMD). The latter typically consist of a housing containing control electronics and a battery, implantable electrodes (or electrode arrays), and cables for the electrical contacting of the electrode with the control electronics. There is a problem here in that, at the beginning of the implantation, the individual components often must not be firmly connected to each other since the electrodes and the electrical unit are located at some distance with respect to each other, where the consequence would be that the complete region in which the cable would extend would have to be cut open. One example of this is deep brain stimulation where the electrodes are located in the brain, the electronics, however, in the thoracic region. In this case, the cables are tunnelled from the electronics towards the electrode and fixed there by means of a plug connection. At present, here, the number of connecting contacts in the plug and its size limit the possible number of electrodes.

Reversibly releasable connectors permit implantation of the components to be electrically connected individually, thereby also creating an option to exchange defective parts, parts in need of improvement, or worn parts. Such implants and connectors are shown e.g. in the publications J. E. Letechipia, P. H. Peckham, M. Gazdik, and B. Smith, "In-line lead connector for use with implanted neuroprosthesis," IEEE Trans. Biomed. Eng., vol. 38, no. 7, pp. 707-709, 1991; M. Cocco, P. Dario, M. Toro, P. Pastacaldi, and R. Sacchetti, "An implantable neural connector incorporating microfabricated components," J. Micromech. Microeng., vol. 3, no. 4, pp. 219-221, 1993; and R. G. Hauser and B. J. Maron, "Lessons from the failure and recall of an implantable cardioverter-defibrillator," (eng), Circulation, vol. 112, no. 13, pp. 2040-2042, 2005.

Depending on the desired number of channels and the desired integration density, the size of the connectors will increase which in turn can negatively affect the surrounding tissue. One disadvantage in the prior art of known connection solutions is that for a reliable contacting, separate spring elements have to be provided for each channel which have a disadvantageous effect on the overall size of the electrical connection. Moreover, by the spring elements, a relatively high introduction force is required which increases proportionally to the number of desired electrical contacts, thus limiting the possible number of provided contacts.

In miniaturized implantable connectors, the electrical insulation between the individual adjacent contacts of different channels moreover causes a problem since, due to the use within the body, a saturated, 100% humid environment prevails. The electrical insulation has to be realized additionally and requires additional materials and forces. Moreover, to ensure sufficient electrical insulation, the distance between adjacent contacts must be comparably long in known connector arrangements, so that the integration density is not sufficiently high. The number of channels is limited for this reason, too, and is maximally 16 in known arrangements.

SUMMARY

An implantable electrical connecting device includes a first elastic multi-ply layer and a second elastic multi-ply layer. The first elastic multi-ply layer has a first electrically conductive layer and a plurality of first electrical contacts electrically conductively connected to the first electrically conductive layer of the first elastic multi-ply layer. The second elastic multi-ply layer has a first electrically conductive layer and a plurality of second electrical contacts electrically conductively connected to the first electrically conductive layer of the second elastic multi-ply layer. The second electrical contacts make contact with the first electrical contacts.

BRIEF DESCRIPTION OF THE DRAWINGS

The invention will now be described by way of example with reference to the accompanying Figures, of which.

DETAILED DESCRIPTION OF THE EMBODIMENT(S)

Figure 1:
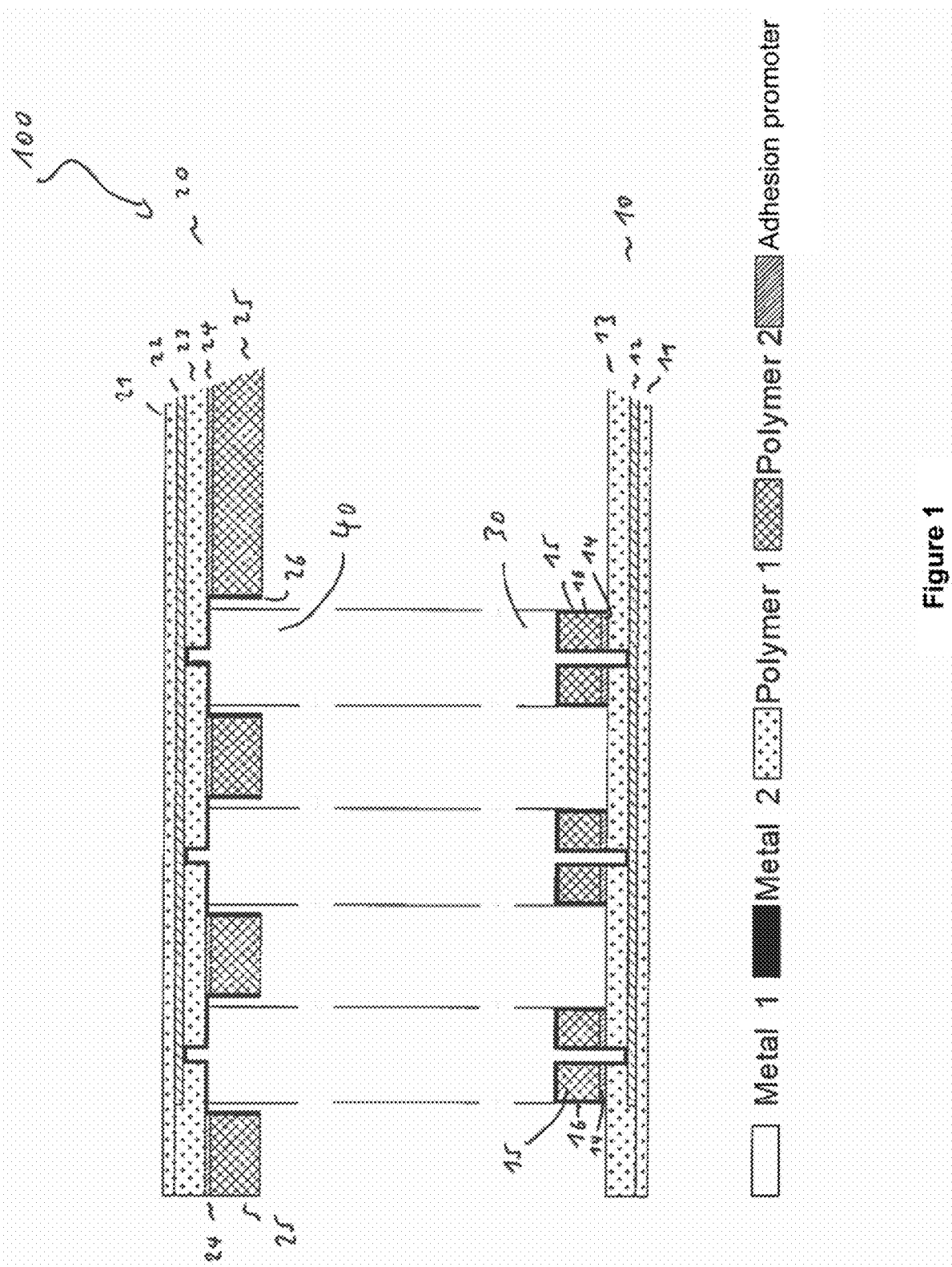
FIG. 1 is a schematic sectional view of a connecting device according to an embodiment.

For a better understanding of the present invention, it will be explained in detail with reference to the exemplary embodiments in the figures. Herein, the same parts are provided with the same reference numerals and the same component designations. Furthermore, some features or feature combinations of the shown and described different embodiments can also represent independent inventive solutions or solutions according to the invention. It will be understood that the embodiments do not exhaust the field of the present invention.

The present invention provides a connecting device for electrically connecting two components that can be or have been implanted into the body of a living being, for example a human. The components can be, for example, electrical components of an implantable stimulation device. For example, one of the components can be or comprise a housing with control and evaluation electronics and a stimulator for generating and supplying electrical pulses, and the other component, which is to be electrically connected to the first one, can consist of or comprise one or a plurality of electrodes or electrode arrays. If reference is made to a layer herein, this can be one single layer, or a plurality of partial layers.

Figure 2:
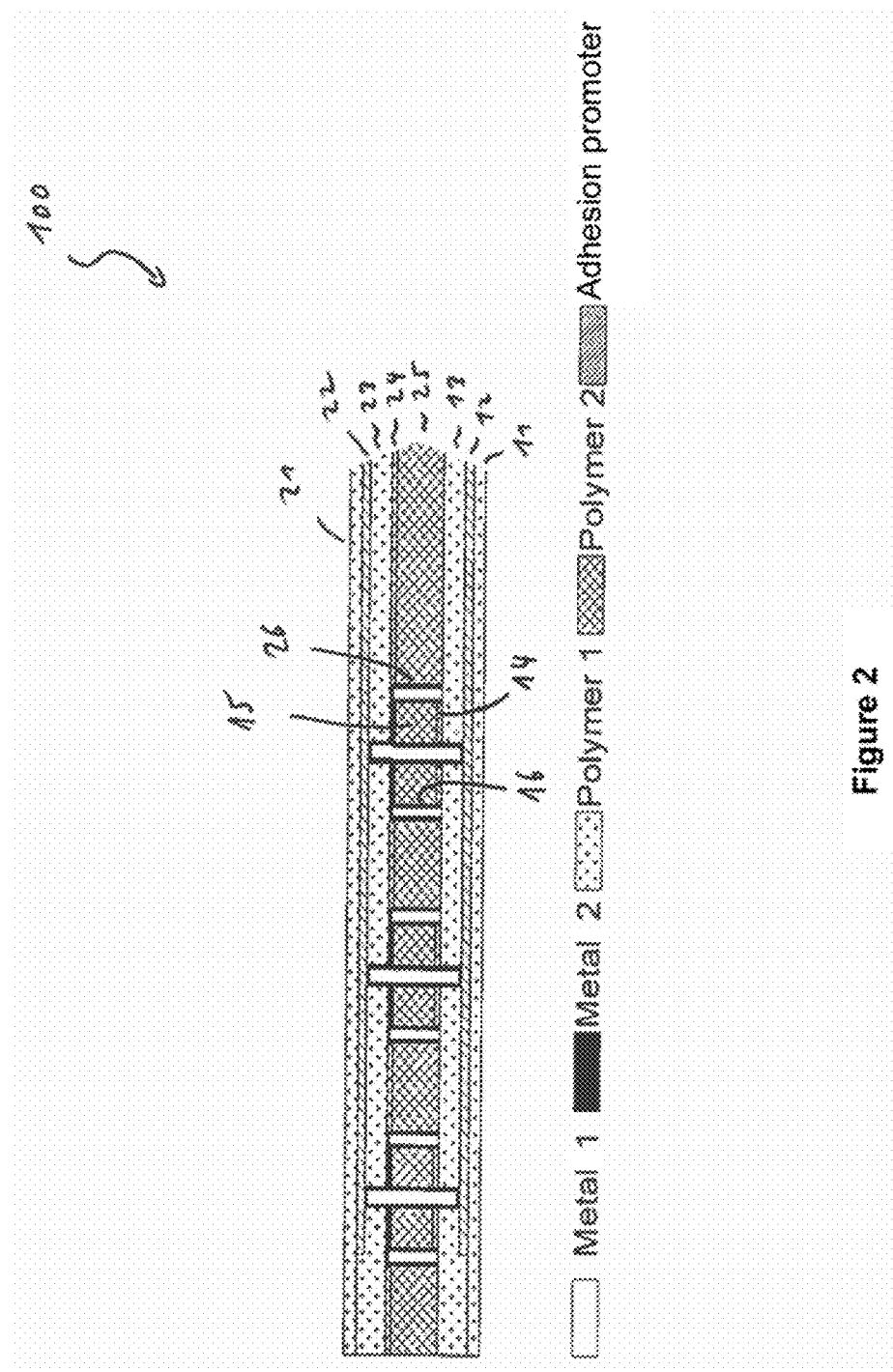
FIG. 2 is a schematic sectional view of the connecting device of FIG. 1 with multi-ply layers arranged on one another.

FIGS. 1 and 2 illustrate a connecting device 100 of an embodiment according to the invention. The connecting device 100 comprises a first elastic multi-ply layer 10 and a second elastic multi-ply layer 20. The first multi-ply layer 10 and the second multi-ply layer 20 are embodied for a plug connection with each other, the first multi-ply layer 10 representing the male part of the plug connection, and the second multi-ply layer 20 representing the female part of the plug connector in the shown embodiment. Before a mechanical and electrical engagement, the two parts are present in a planar form, as is shown in FIGS. 1 and 2. Both the first multi-ply layer 10 and the second multi-ply layer 20 are in this respect embodied elastically, so that they permit a winding up under the influence of a force exerted by a human hand, as described in detail below. The connecting device 100 is an implantable electrical connecting device 100.

The first multi-ply layer 10 comprises, in the embodiment shown in FIGS. 1 and 2, a first dielectric (electrically insulating) layer 11, a first electrically conductive layer 12, a second dielectric layer 13, an adhesion layer 14, a third dielectric layer 15, and a second electrically conductive layer 16. Correspondingly, the second multi-ply layer 20 comprises, in the shown embodiment, a first dielectric layer 21, a first electrically conductive layer 22, a second dielectric layer 23, an adhesion layer 24, a third dielectric layer 25, and a second electrically conductive layer 26. The first electrically conductive layer 12 of the first multi-ply layer 10 and the first electrically conductive layer 22 of the second multi-ply layer 20 are structured so that they provide a plurality of strip conductors (channels) that are mutually electrically insulated. The second electrically conductive layer 16 of the first multi-ply layer 10, and the second electrically conductive layer 26 of the second multi-ply layer 20 represent contact surfaces via which an electrical contacting between the first multi-ply layer 10 and the second multi-ply layer 20 is accomplished in a closed state of the connecting device 100.

Each strip conductor of the structured first electrically conductive layer 12 of the first multi-ply layer 10 and the first electrically conductive layer 22 of the second multi-ply layer 20 can be connected to one or more contact surfaces. Plug-type elevations 30 which are formed by the layers 14, 15 and 16 of the first multi-ply layer 10 fit into the complementary socket-type indentations 40 which are formed by the layers 25 and 26 of the second multi-ply layer 20, as shown in FIGS. 1 and 2. The plug-type elevations 30 in the shown embodiment, and particularly the second electrically conductive layer 16 on each, form first electrical contacts of the first multi-ply layer 10 and the sockets 40, and particularly the second electrically conductive layer 26 on each, form second electrical contacts of the second multi-ply layer 20 designed to make contact with the first electrical contacts.

According to one embodiment, the first dielectric layer 11 of the first multi-ply layer 10, and the second dielectric layer 13 of the first multi-ply layer 10 are formed of an elastic material and can consist of a first polymer or comprise a first polymer. As an alternative, different polymer materials can be used for the first dielectric layer 11 and the second dielectric layer 13. In this case, the provision of a further adhesion layer between these materials is advantageous. The first electrically conductive layer 12 of the first multi-ply layer 10 can consist of a first metal or comprise a first metal, and the second electrically conductive layer 16 of the first multi-ply layer 10 can consist of a second metal or comprise a second metal which can be different from the first metal. The first metal can be platinum, and the second metal can be gold in an embodiment. The two adhesion layers 14 and 24 can be composed of multiple layers, for example of silicon oxide and silicon carbide.

The third dielectric layer 15 of the first multi-ply layer 10 is elastic and can consist of a second polymer or comprise a second polymer, the second polymer being different from the first polymer. Therefore, the adhesion layer 14 is provided for connecting the different polymer materials. As an alternative, the second polymer can be the same as the first polymer, so that the adhesion layer 14 can be eliminated. According to a further embodiment, the plug-type elevations 30 are made in one piece of an electrically conductive (organic and/or non-organic) material, or in multiple layers of electrically conductive (organic and/or non-organic) materials.

The first dielectric layer 21 of the second multi-ply layer 20 and the second dielectric layer 23 of the second multi-ply layer 20 are elastic and can consist of a third polymer or comprise a third polymer. As an alternative, different polymer materials can be used for the first dielectric layer 21 and the second dielectric layer 23. In this case, the provision of a further adhesion layer between these materials is advantageous. The third polymer can be the same as the first polymer which is employed for the first multi-ply layer 10.

The first electrically conductive layer 22 of the second multi-ply layer 20, in an embodiment, can consist of a third metal or comprise a third metal, and the second electrically conductive layer 26 of the second multi-ply layer 20 can consist of a fourth metal or comprise a fourth metal which can be different from the third metal. The third metal can be the same as the first metal which is employed for the first multi-ply layer 10 in another embodiment, and the fourth metal can be the same as the second metal which is employed for the first multi-ply layer 10. The third metal can also be platinum, and the fourth metal can also be gold. The third dielectric layer 25 of the second multi-ply layer 10 is elastic can consist of a fourth polymer or comprise a fourth polymer, the fourth polymer being different from the third polymer. Therefore, the adhesion layer 24 is provided for connecting the different polymer materials. As an alternative, the fourth polymer can be the same as the third polymer, so that the adhesion layer 24 can be eliminated. The third polymer can be the same as the first polymer which is employed for the first multi-ply layer 10, and the fourth polymer can be the same as the second polymer which is employed for the first multi-ply layer 10.

At least some of the polymer layers of the first multi-ply layer 10 and/or the second multi-ply layer 20, in particular the third dielectric layer 25 of the second multi-ply layer 20, can be made of an elastomer, for example a shape memory polymer. For example, the elastomer can have a modulus of elasticity within a range of 10 to 100 MPa at room temperature. The first dielectric layer 11 of the first multi-ply layer 10 and/or the second dielectric layer 13 of the first multi-ply layer 10 and/or the first dielectric layer 21 of the second multi-ply layer 20 and/or the second dielectric layer 23 of the second multi-ply layer 20 can be a polyimide layer or comprise the same. The third dielectric layer 15 of the first multi-ply layer 10 and/or the third dielectric layer 25 of the second multi-ply layer 20 can be a silicone layer, for example a polydimethylsiloxane layer, or comprise the same.

To produce an electrical and mechanical connection between the first multi-ply layer 10 and the second multi-ply layer 20 of the connecting device 100, these multi-ply layers are first of all arranged one upon the other, as is shown in FIG. 2. In this arrangement, the contact surfaces 16 and 26 can, but do not have to, already be in electrical contact with each other.

Figure 3:
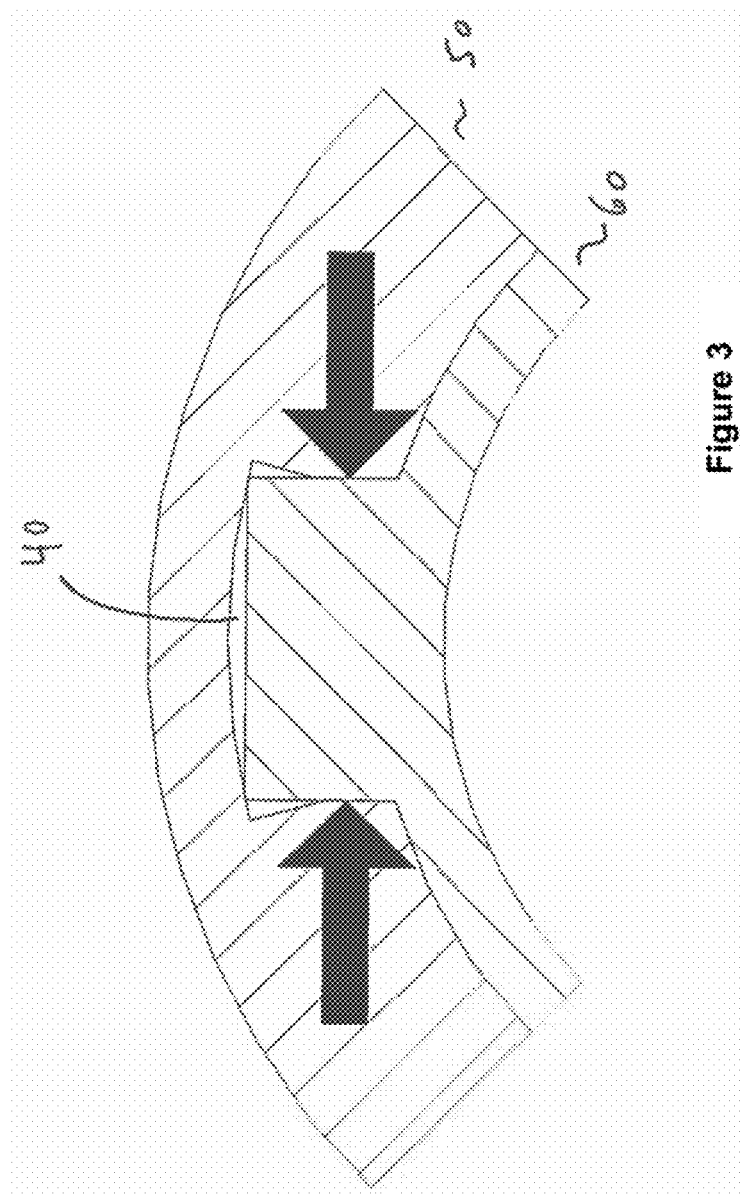
FIG. 3 is detail schematic view of a contact connection of the connecting device of FIG. 1.

The mechanical (positive) engagement (which is not necessarily understood as being without gaps herein) and thereby the stable electrical connection between the first multi-ply layer 10 and the second multi-ply layer 20 are accomplished by together winding up the two multi-ply layers 10 and 20. The winding up can be effected by human hands. The elastic multi-ply layers 10 and 20 permit an elastic deformation, and the positive engagement between the multi-ply layers 10 and 20 is caused by lateral forces that occur during bending/winding up. By bending/winding up, a lateral force is applied by the sockets 40 of the second multi-ply layer 20 at each one of the plug-type elevations 30 of the first multi-ply layer 10, as is illustrated in FIG. 3 by the arrows. For the sake of simplicity, FIG. 3 only shows one polymer layer 50 forming a socket 40 and one contact layer 60 forming a plug-type elevation 30.

Figure 4:
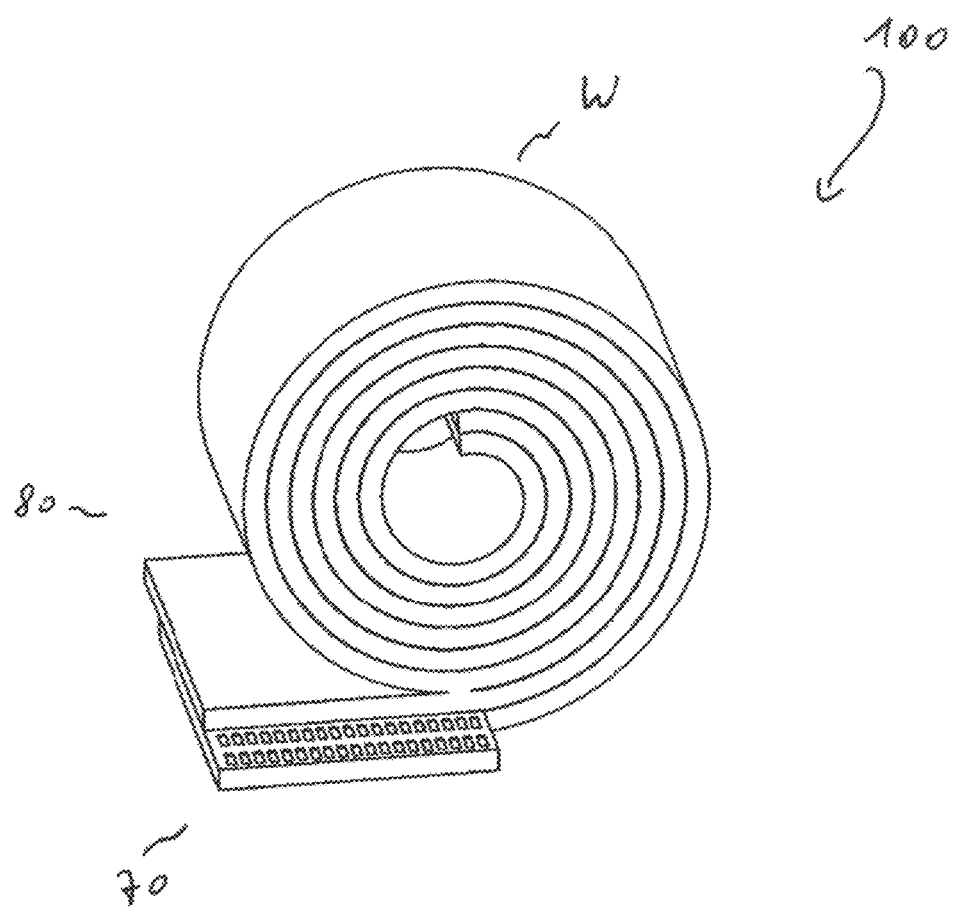
FIG. 4 is a perspective view of a connecting device according to an embodiment after winding.

FIG. 4 illustrates a wound-up connecting device 100 in which the first multi-ply layer 10 and the second multi-ply layer 20 are closed and in electrical contact with each other. The term "wound-up" always comprises completely wound-up (i. e. essentially to the extent mechanically possible without rupture) and partially wound up. The person skilled in the art will be able to adjust the winding corresponding to the application.

As shown in FIG. 4, the winding W passes over, on the one hand, electrically connected with the channels of the structured first electrically conductive layer 22 of the second multi-ply layer 20, into a female contact region 70, and on the other hand, electrically connected with the channels of the structured first electrically conductive layer 12 of the first multi-ply layer 10, into a male contact region 80. At least some of the channels or strip conductors, for example all channels, are in communication with one or, for redundancy purposes, with a plurality of the first or second electrical contacts, respectively. Strip conductors formed by the structured first electrically conductive layer 12 of the first multi-ply layer 10 are connected with (soldering) contact pads formed in the male contact region 80, and strip conductors formed by the structured first electrically conductive layer 22 of the second multi-ply layer 20 are connected with (soldering) contact pads which are formed in the female contact region 70.

In this manner, one of the contact regions 70 and 80 can be connected with a first electrical (implantable/implanted) component, and the other one with a second electrical (implantable/implanted) component. The first component can be, for example, an electrode or an electrode array, and the second component can be, for example, control electronics of an implanted medical device, such as a neurostimulation generator. The components can be connected to the contacts pads at connection regions.

The connection can be accomplished, for example, via multi-wire cables. Upon contacting, the contact pads of the female contact region 70 and of the male contact region 80 can be electrically insulated, for example, by a silicone layer.

One of the two contact regions 70 and 80 can also directly pass over into a desired electrode, for example a detection or stimulation electrode. Furthermore, the two contact regions 70 and 80, or at least one of them, can also be wound up for additionally saving space, whereby the electrical connection to a cable can optionally also be facilitated due to the resulting cylindrical shape.

In contrast to prior art, there is no plug-in connection via spring elements but via the forces acting during winding up. By the winding W, a significant saving of space can be achieved compared to prior art. Moreover, in contrast to prior art, the number of channels made available can be increased, for example to more than sixteen, since no introduction force increasing with the number of channels must be exerted for creating the connection.

Figure 5:
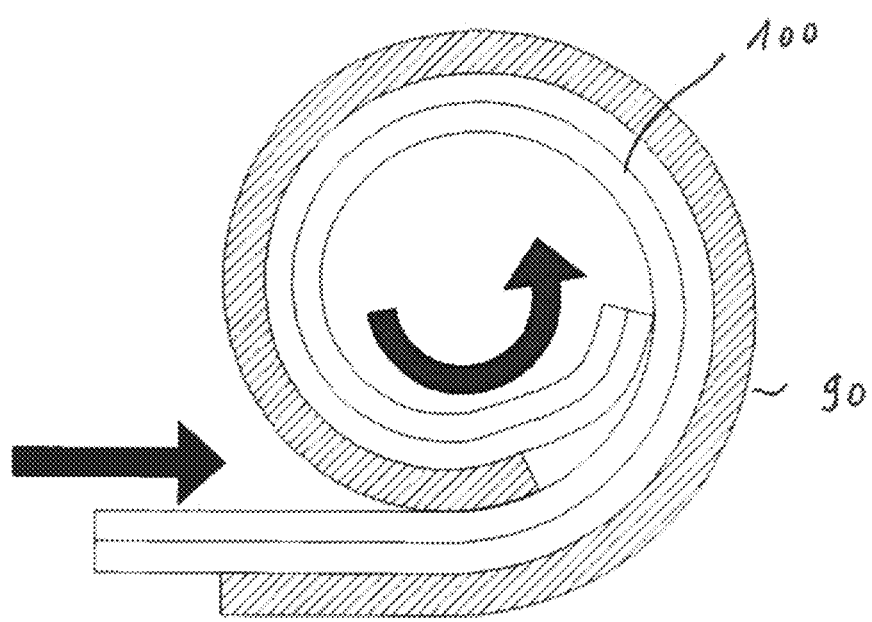
FIG. 5 is a sectional schematic view of a connecting device according to an embodiment with a non-elastic fixing housing.

The winding W shown in FIG. 4 can be secured against an undesired unwinding via suited fixing devices. For example, the readily wound-up connecting device 100 can be secured by a suitably prepared hose which contracts, for example, when heated. The hose can be made, for example, of a polymer material. As an alternative, a suited mechanical clip, for example with a hinge integrated therein and a corresponding locking mechanism, can be provided as a fixing device. A further possibility is illustrated in FIG. 5. Here, a mechanically stable, essentially non-elastic fixing housing 90 which has a helical design inside is provided as a fixing device into which the connecting device 100 can be wound up by shifting it into the arrow direction.

The positioning of the connecting device 100 according to the invention within the body of a patient can be accomplished as follows, for example. In the as-delivered status, the connecting device 100 is already slightly wound-up without a reliable positive engagement and without a reliable electrical contacting to reduce the cross-section for the subcutaneous tunneling. A protecting cover can maintain the loosely wound-up configuration during the subcutaneous tunneling and protect it from external influences. The protecting cover is removed after the subcutaneous tunneling, the two multi-ply layers 10, 20 are unrolled, exactly adjusted with respect to each other and now wound up with a reliable mechanical engagement and a reliable electrical contacting, and the resulting winding is fixed. As an alternative, a connecting device 100 wound up with a reliable mechanical engagement and a reliable electrical contacting could be subcutaneously tunneled to the site of application.

Hereinafter, a manufacturing process for a connecting device is described by way of example, for example for the connecting device 100 shown in FIGS. 1 and 2, according to one embodiment of the present invention with reference to FIGS. 6a and 6b. The first multi-ply layer 10 and the second multi-ply layer 20 can be manufactured using different masks by an essentially equal layering process.

Figure 6A:
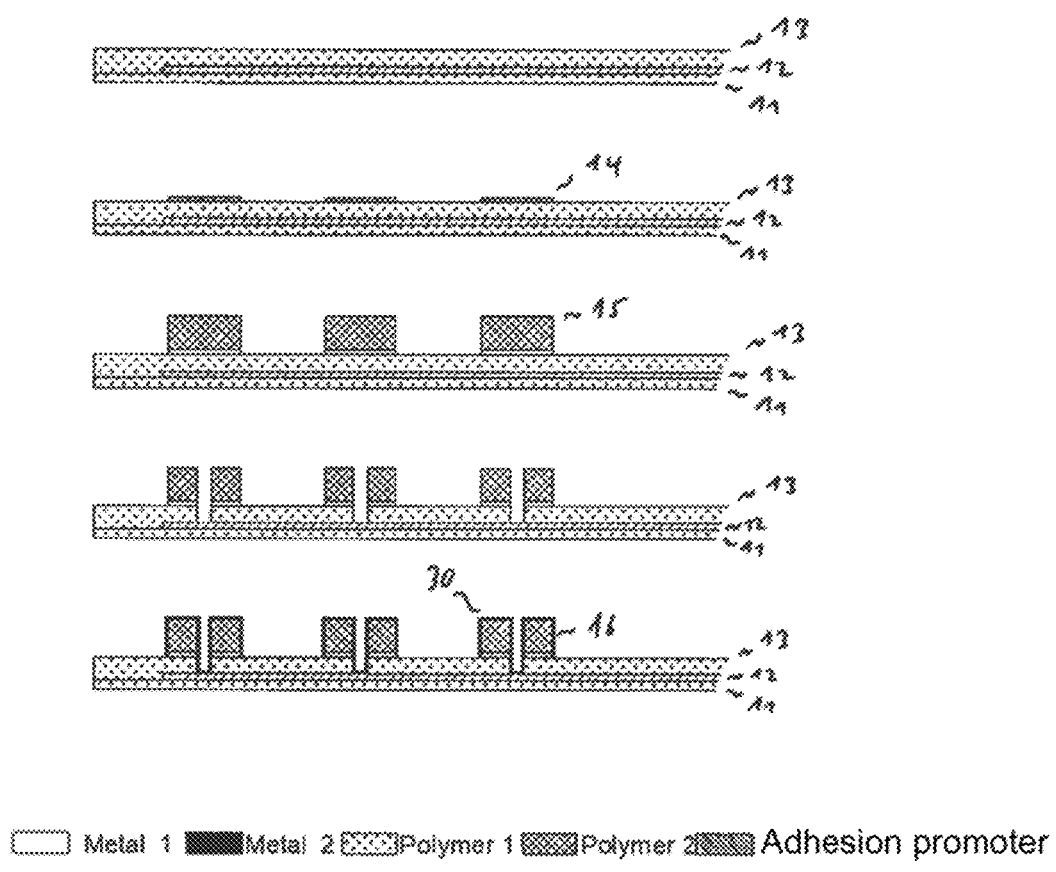
FIG. 6a is a schematic sectional view of a manufacturing process for a first elastic multi-ply layer of a connecting device according to an embodiment.

FIG. 6a shows, in the uppermost row, a manufacturing state for the first multi-ply layer 10 in which the first electrically conductive layer 12 is embodied in the form of a metal layer on the first dielectric layer 11. The first dielectric layer 11 is a polymer layer which is embodied, for example, by a spin-on deposition onto a suited support. The formation of the first electrically conductive layer 12 onto the first dielectric layer 11 is accomplished, for example, by steam deposition. Upon its formation, the first electrically conductive layer 12 is structured for forming strip conductors, for example, by a laser cutting process or by photolithography.

Then, the second dielectric layer 13, which in an embodiment is made from the same polymer material as the first dielectric layer 11, is formed on the configuration formed after the structuring of the first electrically conductive layer 12. This second dielectric layer 13 can also be formed by spin-on deposition. The individual strip conductors of the structured first electrically conductive layer 12 are electrically insulated from each other by the second dielectric layer 13. The two polymer layers 11 and 13 can have thicknesses within a range of 3 to 10 µm, for example 5 µm. The two polymer layers 11 and 13 can consist of polyimide or comprise the same. The metal layer 12 can have a thickness between about 200 and 400 nm, for example 300 nm. The metal layer 12 can consist of an electrically conductive metal, such as platinum, or comprise the same.

As is shown in the second row from top in FIG. 6a, a structured adhesion layer 14 is formed at suited points. A deposition with the aid of a corresponding deposition mask is possible for forming the structured adhesion layer 14. The adhesion layer 14 can comprise a partial layer of silicon dioxide and a partial layer of silicon carbide.

As is shown in the central row of FIG. 6a, in a further manufacturing step, a third dielectric layer 15 of a polymer material which is different from that of the first and second dielectric layers 11 and 13 is formed on the structured adhesion layer 14. For example, a flatly deposited polymer layer can be formed from which then the not desired regions are removed, for example by a laser cutting process. The polymer of the third dielectric layer 15 is to be selected on the basis of the desired elasticity properties in view of a stable connection with the sockets 40 of the second multi-ply layer 20 (see FIGS. 1 and 2). For example, polydimethylsiloxane or a comparable silicone could be suitably selected. The third dielectric layer 15 can result in the plug-type elevations 30.

The structured first electrically conductive layer 12 is exposed for contacting through the structured third dielectric layer 15, the adhesion layer 14, and the second dielectric layer 12, as shown in the second row from the bottom of FIG. 6a, removing a portion of the second dielectric layer 12 to expose a portion of the first electrically conductive layer 12. Finally, the second electrically conductive layer 16 of metal, for example gold, is embodied in contact with the structured first electrically conductive layer 12 and on and at side walls of the third dielectric layer 15 (see lowermost row of FIG. 6a). The formation of the second electrically conductive layer 16 can be accomplished by a chemical steam deposition process. The second electrically conductive layer 16 forms the first electrical contacts over the second dielectric layer 13 and in electrically conductive contact with the first electrically conductive layer 11. The thus formed structure can then be released from the support for further use.

While in the described example, the plug-type elevations 30 are formed of a polymer and a metal layer, they can alternatively also be formed of other organic and/or inorganic, electrically conductive materials in single- or multi-ply designs.

The formation of the second multi-ply layer 20 is accomplished similar to that of the first multi-ply layer 10. First of all, the stack of layers shown in the uppermost row of FIG. 6b is formed in the same manner. The stack of layers comprises the first dielectric layer 21, the first electrically conductive layer 22, and the second dielectric layer 23. Materials and layer thicknesses can here be selected as in the formation of the first multi-ply layer 10. Then, the structured adhesion layer 24, possibly also comprising a partial layer of silicon dioxide and a partial layer of silicon carbide, is formed. Structuring is accomplished complementary to that of the structured adhesion layer 14 of the first multi-ply layer 10 (see second row from above in FIG. 6b). On the structured adhesion layer 24, a further polymer layer 25 is formed as the third dielectric layer 25, as is represented in the central row of FIG. 6b. The selection of the polymer material is determined by the elasticity properties which have to take care of a stable connection with the plug-type elevations 30 of the first multi-ply layer 10, so that during the bending/winding onto the finally introduced plug-type elevations 30 of the first multi-ply layer 10, a lateral force sufficient for the positive engagement is exerted (compare FIGS. 2 and 3).

Figure 6B:
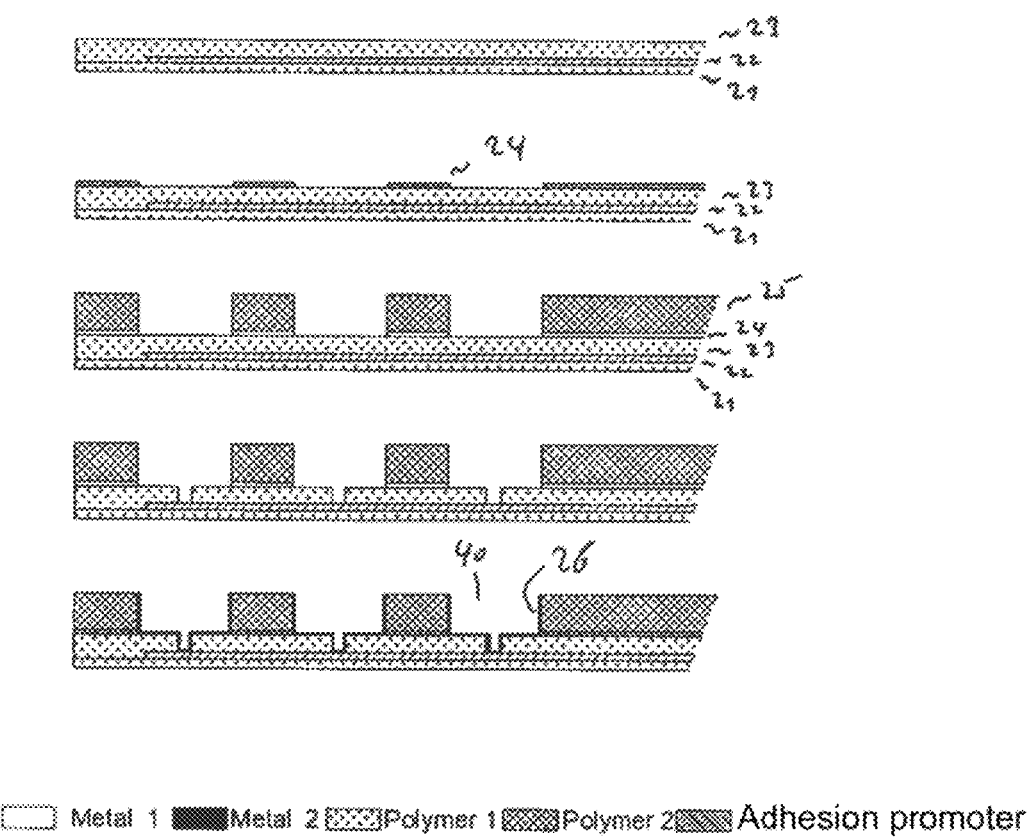
FIG. 6b is a schematic sectional view of a manufacturing process for a second elastic multi-ply layer of a connecting device according to an embodiment.

The structured first electrically conductive layer 22 is exposed for contacting through the structured third dielectric layer 25 and the second dielectric layer 23, as shown in the second row from the bottom of FIG. 6b. A portion of the second dielectric layer 23 is removed to expose a portion of the first electrically conductive layer 22. Finally, the second electrically conductive layer 26 of metal, for example gold, is formed in contact with the structured first electrically conductive layer 22 and at side walls of the third dielectric layer 25 and over the second dielectric layer 23, so that socket-type electrical contact points 40 to the structured first electrically conductive layer 22 are formed (see lowermost row of FIG. 6b) which contact, in the closed state of the connecting device 100 (see FIG. 3), the plug-type elevations 30 of the first multi-ply layer 10. The second electrically conductive layer 26 forms the second electrical contacts partially over the second dielectric layer 23 and in electrically conductive contact with the first electrically conductive layer 22.

The implantable connecting device 100 permits a secure electrical connection of implanted components with a low space demand and a channel density increased compared to prior art.

What is claimed is:

1. An implantable electrical connecting device, comprising:
   a first elastic multi-ply layer having a first electrically conductive layer, a plurality of first electrical contacts electrically conductively connected to the first electrically conductive layer of the first elastic multi-ply layer, a first dielectric layer on which the first electrically conductive layer of the first elastic multi-ply layer is structured, a second dielectric layer formed on the first electrically conductive layer of the first elastic multi-ply layer, a second electrically conductive layer forming the first electrical contacts, and a third dielectric layer on which the second electrically conductive layer of the first elastic multi-ply layer is partially formed; and
   a second elastic multi-ply layer having a first electrically conductive layer and a plurality of second electrical contacts electrically conductively connected to the first electrically conductive layer of the second elastic multi-ply layer, the second electrical contacts make contact with the first electrical contacts.

2. The implantable electrical connecting device of claim 1, wherein the first elastic multi-ply layer and the second elastic multi-ply layer positively engage each other.

3. The implantable electrical connecting device of claim 1, wherein the first electrical contacts of the first elastic multi-ply layer are a plurality of plug-type elevations.

4. The implantable electrical connecting device of claim 3, wherein the second electrical contacts of the second elastic multi-ply layer are a plurality of socket-type indentations.

5. The implantable electrical connecting device of claim 1, wherein the third dielectric layer of the first elastic multi-ply layer comprises a polymer material or consists of the polymer material.

6. The implantable electrical connecting device of claim 5, wherein the polymer material comprises an elastomer or a memory polymer or consists of the elastomer or the memory polymer.

7. The implantable electrical connecting device of claim 1, wherein the second elastic multi-ply layer includes:
  a first dielectric layer on which the first electrically conductive layer of the second elastic multi-ply layer is structured;
  a second dielectric layer formed on the first electrically conductive layer of the second elastic multi-ply layer; and
  a second electrically conductive layer forming the second electrical contacts.

8. The implantable electrical connecting device of claim 7, wherein the second elastic multi-ply layer has a third dielectric layer on which the second electrically conductive layer of the second elastic multi-ply layer is partially formed.

9. The implantable electrical connecting device of claim 8, wherein the third dielectric layer of the second elastic multi-ply layer comprises a polymer material or consists of the polymer material.

10. The implantable electrical connecting device of claim 9, wherein the polymer material comprises an elastomer or a memory polymer or consists of the elastomer or the memory polymer.

11. The implantable electrical connecting device of claim 1, wherein the first elastic multi-ply layer and the second elastic multi-ply layer are at least partially wound up together.

12. A method of manufacturing an implantable connecting device, comprising:
  forming a first elastic multi-ply layer, including:
    forming a first dielectric layer;
    forming a first electrically conductive layer on the first dielectric layer of the first elastic multi-ply layer;
    forming a second dielectric layer on the first electrically conductive layer of the first elastic multi-ply layer;
    removing a portion of the second dielectric layer to expose a portion of the first electrically conductive layer of the first elastic multi-ply layer; and
    forming a plurality of first electrical contacts partially over the second dielectric layer of the first elastic multi-ply layer and in electrical contact with the first electrically conductive layer of the first elastic multi-ply layer, forming the first electrical contacts includes forming a third dielectric layer over the second dielectric layer of the first elastic multi-ply layer, and forming a second electrically conductive layer partially over the third dielectric layer of the first elastic multi-ply layer and in electrical contact with the first electrically conductive layer of the first elastic multi-ply layer; and
  forming a second elastic multi-ply layer, including:
    forming a further first dielectric layer;
    forming a further first electrically conductive layer on the further first dielectric layer of the second elastic multi-ply layer;
    forming a further second dielectric layer on the further first electrically conductive layer of the second elastic multi-ply layer;
    removing a portion of the further second dielectric layer to expose a portion of the further first electrically conductive layer of the second elastic multi-ply layer; and
    forming a plurality of second electrical contacts partially over the further second dielectric layer of the second elastic multi-ply layer and in electrical contact with the further first electrically conductive layer of the second elastic multi-ply layer.

13. The method of claim 12, wherein forming the first electrical contacts includes removing a portion of the third dielectric layer of the first elastic multi-ply layer to expose the portion of the first electrically conductive layer of the first elastic multi-ply layer.

14. The method of claim 12, wherein forming the second electrical contacts includes forming a further third dielectric layer over the further second dielectric layer of the second elastic multi-ply layer, and removing a portion of the further third dielectric layer to form a plurality of socket-type indentations in the further second dielectric layer of the second elastic multi-ply layer.

15. The method of claim 14, wherein forming the second electrical contacts includes forming a further second electrically conductive layer at a plurality of side walls of the socket-type indentations and in electrical contact with the further first electrically conductive layer of the second elastic multi-ply layer.

16. The method of claim 12, further comprising:
  arranging the first elastic multi-ply layer and the second elastic multi-ply layer upon one another; and
  winding up the first elastic multi-ply layer and the second elastic multi-ply layer arranged upon one another.

17. A method, comprising:
  providing an implantable electrical connecting device including a first elastic multi-ply layer having a first electrically conductive layer, a plurality of first electrical contacts electrically conductively connected to the first electrically conductive layer of the first elastic multi-ply layer, a first dielectric layer on which the first electrically conductive layer of the first elastic multi-ply layer is structured, a second dielectric layer formed on the first electrically conductive layer of the first elastic multi-ply layer, a second electrically conductive layer forming the first electrical contacts, and a third dielectric layer on which the second electrically conductive layer of the first elastic multi-ply layer is partially formed, and a second elastic multi-ply layer having a first electrically conductive layer and a plurality of second electrical contacts electrically conductively connected to the first electrically conductive layer of the second elastic multi-ply layer, the second electrical contacts make contact with the first electrical contacts;
  arranging the first elastic multi-ply layer and the second elastic multi-ply layer upon one another; and
  winding up the first elastic multi-ply layer and the second elastic multi-ply layer arranged upon one another.

18. An implantable electrical connecting device, comprising:
  a first elastic multi-ply layer having a first electrically conductive layer and a plurality of first electrical contacts electrically conductively connected to the first electrically conductive layer of the first elastic multi-ply layer; and
  a second elastic multi-ply layer having a first electrically conductive layer, a plurality of second electrical contacts electrically conductively connected to the first electrically conductive layer of the second elastic multi-ply layer, the second electrical contacts make contact with the first electrical contacts, a first dielectric layer on which the first electrically conductive layer of the second elastic multi-ply layer is structured, a second dielectric layer formed on the first electrically conductive layer of the second elastic multi-ply layer, a second electrically conductive layer forming the second electrical contacts, and a third dielectric layer on which the second electrically conductive layer of the second elastic multi-ply layer is partially formed.

19. The implantable electrical connecting device of claim 18, wherein the third dielectric layer of the second elastic multi-ply layer comprises a polymer material or consists of the polymer material.

20. The implantable electrical connecting device of claim 19, wherein the polymer material comprises an elastomer or a memory polymer or consists of the elastomer or the memory polymer.

21. A method of manufacturing an implantable connecting device, comprising:
    forming a first elastic multi-ply layer, including:
        forming a first dielectric layer;
        forming a first electrically conductive layer on the first dielectric layer of the first elastic multi-ply layer;
        forming a second dielectric layer on the first electrically conductive layer of the first elastic multi-ply layer;
        removing a portion of the second dielectric layer to expose a portion of the first electrically conductive layer of the first elastic multi-ply layer; and
        forming a plurality of first electrical contacts partially over the second dielectric layer of the first elastic multi-ply layer and in electrical contact with the first electrically conductive layer of the first elastic multi-ply layer; and
    forming a second elastic multi-ply layer, including:
        forming a further first dielectric layer;
        forming a further first electrically conductive layer on the further first dielectric layer of the second elastic multi-ply layer;
        forming a further second dielectric layer on the further first electrically conductive layer of the second elastic multi-ply layer;
        removing a portion of the further second dielectric layer to expose a portion of the further first electrically conductive layer of the second elastic multi-ply layer; and
        forming a plurality of second electrical contacts partially over the further second dielectric layer of the second elastic multi-ply layer and in electrical contact with the further first electrically conductive layer of the second elastic multi-ply layer, forming the second electrical contacts includes forming a further third dielectric layer over the further second dielectric layer of the second elastic multi-ply layer, and removing a portion of the further third dielectric layer to form a plurality of socket-type indentations in the further second dielectric layer of the second elastic multi-ply layer.

22. The method of claim 21, wherein forming the second electrical contacts includes forming a further second electrically conductive layer at a plurality of side walls of the socket-type indentations and in electrical contact with the further first electrically conductive layer of the second elastic multi-ply layer.

* * * * *